(12) United States Patent
Karunasiri et al.

(10) Patent No.: US 11,213,688 B2
(45) Date of Patent: Jan. 4, 2022

(54) UTILIZATION OF A NON-WEARABLE COIL TO REMOTELY POWER A COCHLEAR IMPLANT FROM A DISTANCE

(71) Applicant: Advanced Bionics AG, Staefa (CH)

(72) Inventors: R. Tissa Karunasiri, Valencia, CA (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 293 days.

(21) Appl. No.: 16/370,983

(22) Filed: Mar. 30, 2019

(65) Prior Publication Data
US 2020/0306548 A1 Oct. 1, 2020

(51) Int. Cl.
*A61N 1/378* (2006.01)
*A61N 1/36* (2006.01)
*A61N 1/05* (2006.01)
*H04R 25/00* (2006.01)

(52) U.S. Cl.
CPC ....... *A61N 1/3787* (2013.01); *A61N 1/36038* (2017.08); *A61N 1/0541* (2013.01); *H04R 25/30* (2013.01)

(58) Field of Classification Search
None
See application file for complete search history.

(56) References Cited

U.S. PATENT DOCUMENTS

| | | | |
|---|---|---|---|
| 7,520,851 B2 | 4/2009 | Davis et al. | |
| 7,612,655 B2 | 11/2009 | Kolz et al. | |
| 7,751,899 B1 | 7/2010 | Karunasiri | |
| 8,760,284 B2 | 6/2014 | Petersen et al. | |
| 9,124,991 B2 | 9/2015 | Van Gerwen | |
| 9,522,282 B2 | 12/2016 | Chow et al. | |
| 9,968,781 B2 | 5/2018 | Roehrlein et al. | |
| 2008/0194953 A1 | 8/2008 | Kerber | |

(Continued)

FOREIGN PATENT DOCUMENTS

WO 2016/205589 12/2016

OTHER PUBLICATIONS

Kakkar, et al., Low Power Architecture For Cochlear Implant, https://www.researchgate.net/publication/50257309_Low_Power_Architecture_For_Cochlear_Implant, International Journal of Engineering Science and Technology, vol. 2 (2), 2010, 51-58, Feb. 28, 2010.

*Primary Examiner* — Allen Porter
*Assistant Examiner* — James Moss
(74) *Attorney, Agent, or Firm* — ALG Intellectual Property, LLC

(57) ABSTRACT

An exemplary system includes a sound processor configured to wirelessly communicate, while operating in a first mode, with a cochlear implant by way of a wearable headpiece coil configured to be worn on a head of a recipient of the cochlear implant, a non-wearable coil configured to be located away from the recipient, and an interface device configured to provide operating power to the non-wearable coil and communicatively couple to the sound processor while the sound processor is operating in a second mode. While the sound processor is coupled to the interface device and operating in the second mode, the non-wearable coil is configured to provide radio frequency (RF) power to the cochlear implant to keep the cochlear implant listening for commands from the sound processor.

17 Claims, 9 Drawing Sheets

(56) References Cited

U.S. PATENT DOCUMENTS

| | | | |
|---|---|---|---|
| 2009/0216296 A1* | 8/2009 | Meskens | A61N 1/36036 607/57 |
| 2010/0087700 A1 | 4/2010 | Zimmerling | |
| 2010/0121411 A1* | 5/2010 | Hochmair | A61N 1/36036 607/55 |
| 2010/0174344 A1* | 7/2010 | Dadd | A61N 5/0601 607/57 |
| 2012/0150259 A1* | 6/2012 | Meskens | A61N 1/37223 607/57 |
| 2013/0109909 A1* | 5/2013 | van Gerwen | H04R 25/554 600/25 |
| 2013/0261703 A1* | 10/2013 | Chow | A61N 1/40 607/61 |
| 2013/0343584 A1 | 12/2013 | Bennett et al. | |
| 2014/0379047 A1* | 12/2014 | Meskens | A61N 1/3787 607/57 |
| 2015/0358710 A1* | 12/2015 | Hartley | A61N 1/36038 381/315 |
| 2016/0021468 A1* | 1/2016 | Karunasiri | A61N 1/36038 381/314 |
| 2016/0375242 A1* | 12/2016 | Roehrlein | A61N 1/37223 607/57 |
| 2016/0375243 A1 | 12/2016 | Roehrlein et al. | |
| 2017/0001008 A1* | 1/2017 | Hunt | A61N 1/36036 |
| 2017/0127196 A1 | 5/2017 | Blum et al. | |
| 2017/0291027 A1 | 10/2017 | Gordon et al. | |
| 2018/0103330 A1 | 4/2018 | Balslev | |
| 2018/0110984 A1 | 4/2018 | Van Den Heuvel | |
| 2018/0139545 A1 | 5/2018 | Goorevich et al. | |
| 2019/0054305 A1* | 2/2019 | Janssen | H04R 25/305 |
| 2020/0324127 A1* | 10/2020 | Leigh | A61N 1/3787 |

* cited by examiner

UTILIZATION OF A NON-WEARABLE COIL TO REMOTELY POWER A COCHLEAR IMPLANT FROM A DISTANCE

BACKGROUND INFORMATION

A conventional cochlear implant implanted within a recipient receives operating power from an external sound processor via a transcutaneous link between a coil included in a headpiece externally worn on the head of the recipient and an implanted coil included in or otherwise connected to the cochlear implant. Hence, when the recipient removes the headpiece from his or her head (e.g., before going to sleep), the cochlear implant is not powered and cannot provide stimulation representative of sound to the recipient. This may result in the recipient not being aware of important audible notifications (e.g., fire alarms, security alarms, etc.) that may occur while the recipient is not wearing his or her headpiece.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
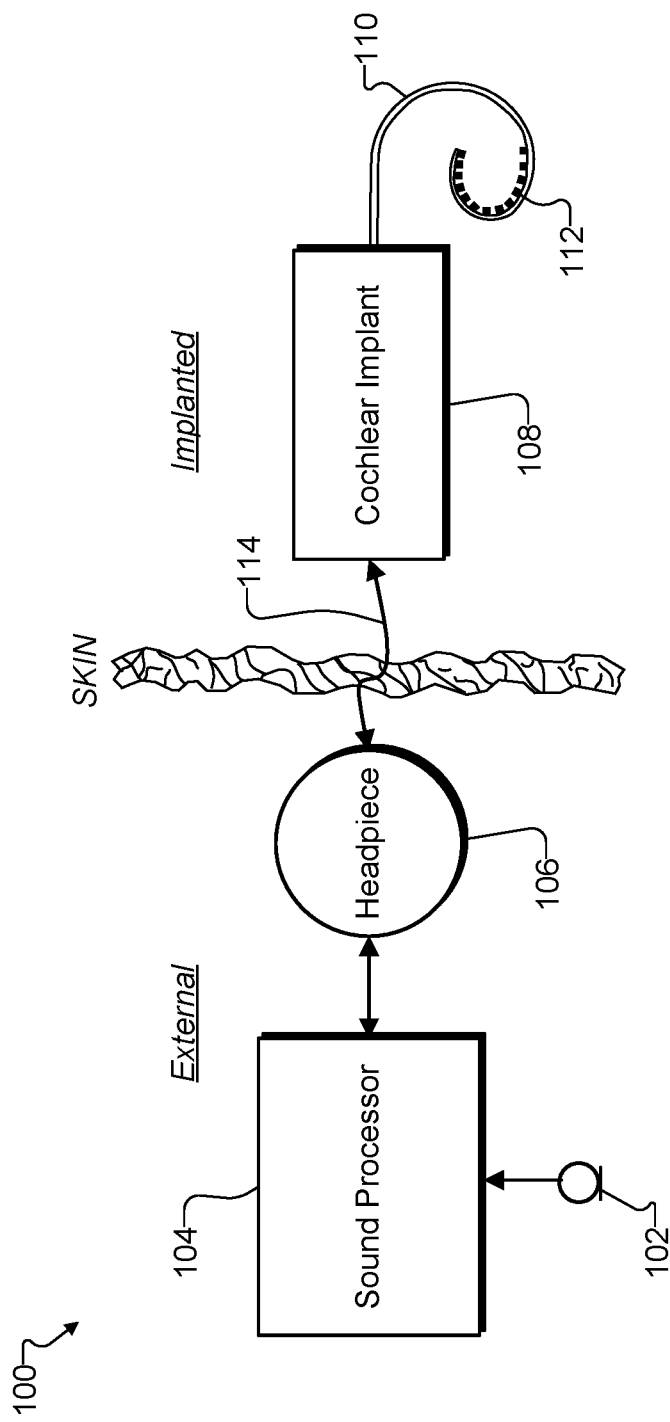
FIG. 1 illustrates an exemplary cochlear implant system according to principles described herein.

Systems and methods that facilitate utilization of a non-wearable coil to remotely power a cochlear implant from a distance are described herein. As will be described in more detail below, an exemplary system includes a sound processor configured to wirelessly communicate, while operating in a first mode, with a cochlear implant by way of a wearable headpiece coil configured to be worn on a head of a recipient of the cochlear implant, a non-wearable coil configured to be located away from the recipient, and an interface device configured to provide operating power to the non-wearable coil and communicatively couple to the sound processor while the sound processor is operating in a second mode. While the sound processor is coupled to the interface device and operating in the second mode, the non-wearable coil is configured to provide RF power to the cochlear implant to keep the cochlear implant listening for commands from the sound processor.

To illustrate, a recipient of a cochlear implant may remove a wearable headpiece coil (e.g., a coil included with a headpiece) from the head of the recipient prior to going to bed. The recipient may also remove a sound processor configured to control the cochlear implant from behind his or her ear and connect the sound processor to an interface device (e.g., a charging cradle). In this configuration, the interface device may provide operating power to a non-wearable coil configured to be located away from the recipient (e.g., a coil incorporated into a picture frame located in the same room where the recipient is sleeping). The non-wearable coil is configured to provide RF power to the cochlear implant to keep the cochlear implant listening for commands for commands from the sound processor while the sound processor and headpiece coil are not being worn by the recipient.

While the wearable headpiece coil and sound processor are not being worn by the recipient, the sound processor may monitor (e.g., with a microphone associated with the sound processor) an environment of the recipient for ambient sound that has a predetermined characteristic (e.g., a loudness level above a certain threshold, a particular frequency, etc.). When the sound processor detects the ambient sound, the sound processor may transmit a command to the cochlear implant by way of the interface device and the non-wearable coil. The command may direct the cochlear implant to apply stimulation (e.g., stimulation representative of the ambient sound and/or stimulation representative of an alert) to the recipient.

By utilizing a non-wearable coil, it is possible to provide operating power and/or commands to a cochlear implant from a distance even when a wearable headpiece coil is not worn on the head of the recipient. In this manner, the systems and methods described herein may facilitate providing the recipient of a cochlear implant with important alerts, the perception of sound, etc. at times when the recipient of the cochlear implant would otherwise not be able to perceive sound. In addition, the systems and methods described herein may improve the recipient's quality of life by reducing or preventing certain auditory symptoms (e.g., tinnitus) from being experienced by the recipient while a headpiece is not attached to the head of the recipient. Other benefits of the systems and methods described herein will be made apparent herein.

FIG. 1 illustrates an exemplary cochlear implant system 100. As shown, cochlear implant system 100 may include various components configured to be located external to a recipient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

Headpiece 106 may be communicatively coupled to sound processor 104 and may include various components configured to facilitate selective wireless coupling of sound processor 104 to cochlear implant 108. To this end, headpiece 106 may be configured to be affixed to the recipient's head so as to transmit commands (e.g., stimulation parameters) and/or RF power wirelessly between sound processor 104 and cochlear implant 108 via a wireless communication link 114 (which may include a bi-directional communication link and/or one or more dedicated uni-directional communication links as may serve a particular implementation). Exemplary components that may be included in Headpiece 106 to facilitate wireless communication link 114 are described herein.

In some examples, sound processor 104 may wirelessly transmit stimulation parameters (e.g., in the form of data words included in a forward telemetry sequence) and/or RF power to cochlear implant 108 by way of wireless communication link 114 between headpiece 106 and cochlear implant 108.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the recipient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") or sequentially by way of multiple electrodes 112.

Figure 2:
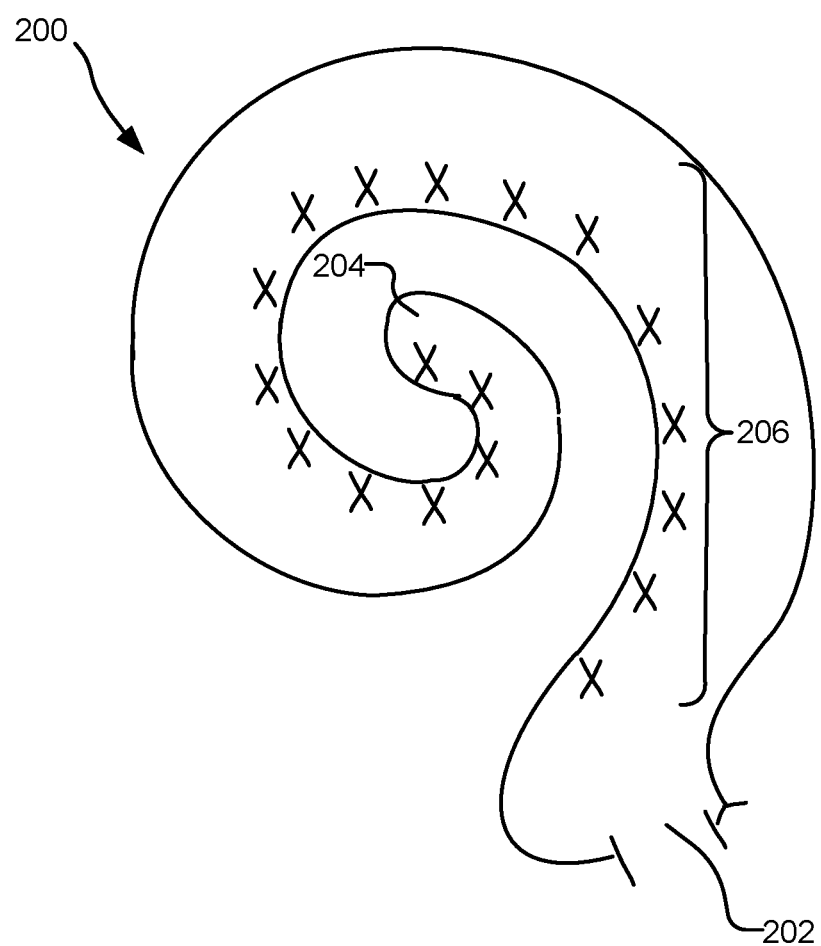
FIG. 2 illustrates a schematic structure of the human cochlea.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
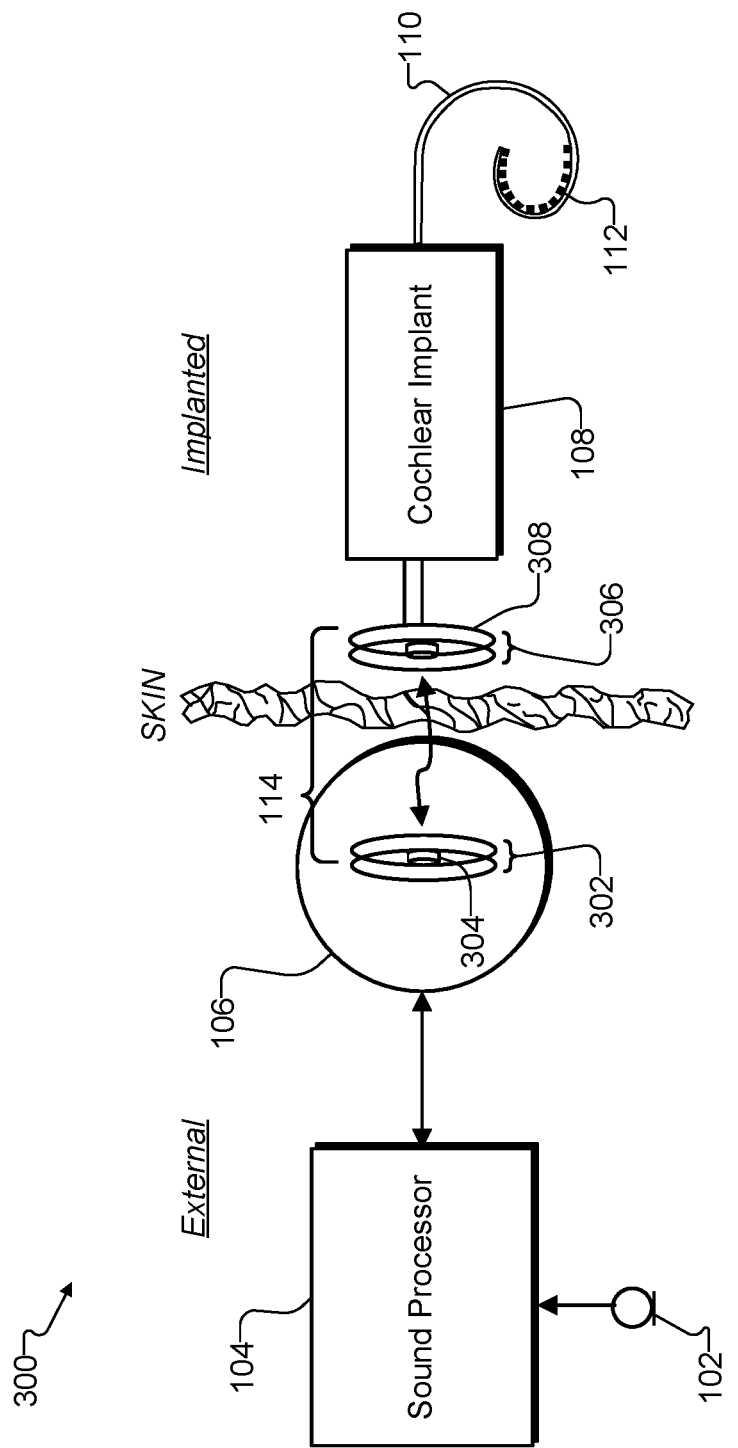
FIG. 3 illustrates an exemplary configuration of the cochlear implant system shown in FIG. 1 according to principles described herein.

FIG. 3 shows an exemplary configuration 300 of cochlear implant system 100 in which a headpiece coil 302 (also referred to as an external antenna) and a headpiece magnet 304 are included as components within headpiece 106. FIG. 3 also shows an internal coil 306 and a cochlear implant magnet 308 that are implanted within the recipient. As shown in FIG. 3, wearable headpiece coil 302 is provided external to the recipient and communicatively couples with internal coil 306, which is communicatively coupled to cochlear implant 108. Wearable headpiece coil 302 is configured to transcutaneously transmit RF power and/or commands to cochlear implant 108 by way of internal coil 306. Headpiece magnet 304 is configured to interact with cochlear implant magnet 308 so as to maintain headpiece 106 at a predefined position with respect to cochlear implant 108 while headpiece 106 is worn on the head of the recipient. Although FIG. 3 shows headpiece 106 and wearable headpiece coil 302 as being separated slightly from the skin of the recipient, it is understood that the interaction between headpiece magnet 304 and cochlear implant magnet 308 causes headpiece 106 to be in direct contact with and not separated from the skin of the recipient while headpiece 106 is at the predefined position.

In addition to or as an alternative to wearable headpiece coil 302, a non-wearable coil may be used in certain examples to provide additional RF power and/or commands to cochlear implant 108 from a distance. In certain examples, the non-wearable coil may provide RF power and/or commands to cochlear implant 108 while wearable headpiece coil 302 is not worn on the head of the recipient. To illustrate, FIG. 4 shows an exemplary configuration 400 in which RF power and/or commands are provided to cochlear implant 108 by way of a non-wearable coil 402 that is communicatively coupled to an interface device 404.

Figure 4:
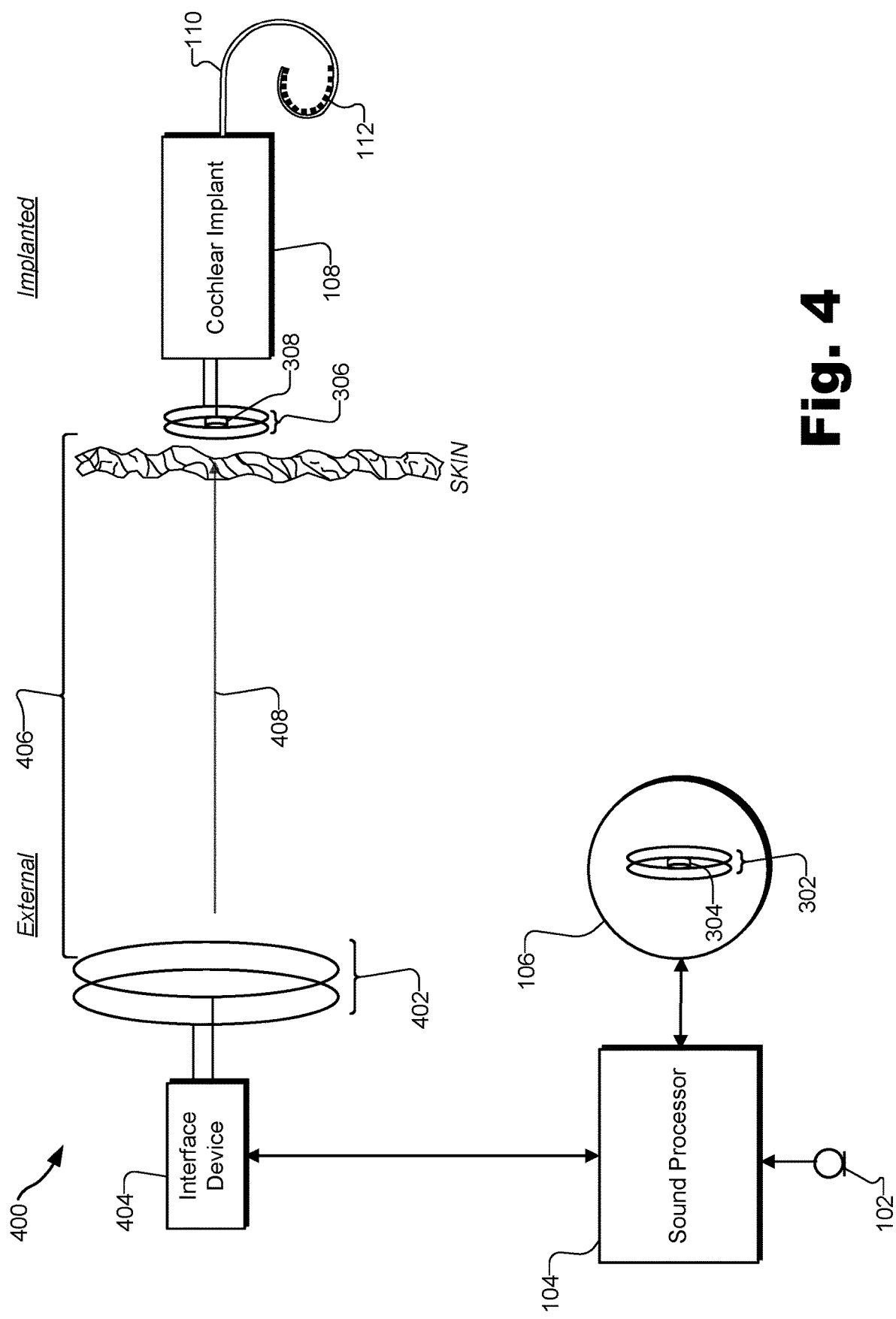
FIG. 4 illustrates an exemplary implementation in which a non-wearable coil is used to provide radio frequency ("RF") power to a cochlear implant according to principles described herein.

In FIG. 4, wearable headpiece coil 302 is positioned away from the recipient such that wearable headpiece coil 302 is not communicatively coupled with cochlear implant coil 306. In this configuration, non-wearable coil 402 is configured to provide RF power and/or commands over a distance 406 by way of a wireless communication link 408. In certain examples, interface device 404 may be configured to perform uni-directional communication with the cochlear implant 108 by way of non-wearable coil 402. That is, due to distance 406, cochlear implant 108 may not have sufficient power to use cochlear implant coil 306 to communicate back with interface device 404. In alternative configurations, communication between non-wearable coil 402 and cochlear implant 108 is bi-directional.

The distance that non-wearable coil 402 may be positioned away from internal coil 306 and still provide RF power and/or commands by way of wireless communication link 408 depends on the size of non-wearable coil 402 and the amount of operating power provided to non-wearable coil 402. In general, the larger the size of non-wearable coil 402 the greater the distance that the RF power and/or commands may be transmitted by way of wireless communication link 408. As such, non-wearable coil 402 may have a first size and cochlear implant coil 306 may have a second size, the first size being larger than the second size.

In the example shown in FIG. 4, non-wearable coil 402 is approximately two times larger than cochlear implant coil 306. However, non-wearable coil may be any suitable amount larger than cochlear implant coil 306 as may serve a particular implementation. In certain examples, non-wearable coil 402 may be three or more times larger than cochlear implant coil 306.

Unlike wearable headpiece coil 302, non-wearable coil 402 is not configured to be worn on the head of the recipient of cochlear implant 108. As such, as shown in FIG. 4, non-wearable coil 402 does not include a magnet configured to interact with magnet 308 that is implanted within the recipient.

Non-wearable coil 402 may be implemented in any suitable manner as may serve a particular implementation. For example, non-wearable coil 402 may be wound around a periphery of a computer monitor, a picture frame, or any other suitable object that may be located within the environment of the recipient. In certain examples, non-wearable coil 402 may be incorporated within a pillow or a mattress of a bed of the recipient. In certain alternative examples, non-wearable coil 402 may be incorporated as part of a stand-alone device that may be provided, for example, on a nightstand adjacent to where the recipient may sleep. In such examples, the stand-alone device including non-wearable coil 402 may be foldable to facilitate the recipient easily transporting non-wearable coil 402, for example, when the recipient travels.

Non-wearable coil 402 is shown in FIG. 4 as having two coils that are coiled in an oval shape. However, it is understood that non-wearable coil 402 may have any suitable shape, size, and/or number of coils as may serve a particular implementation. For example, the coils included in non-wearable coil 402 may be coiled in a square shape, a rectangular shape, a triangular shape, a circular shape or any other suitable shape in certain implementations.

Interface device 404 is configured to provide operating power to non-wearable coil 402 and to communicatively couple to sound processor 104. Interface device 404 may provide the operating power to non-wearable coil 402 in any suitable manner. In certain examples, interface device 404 may be configured to generate and provide the operating power to non-wearable coil 402. Additionally or alternatively, sound processor 104 may provide the operating power to interface device 404, which then passes the operating power on to non-wearable coil 402.

Interface device 404 is configured to communicatively couple to sound processor 104 in any suitable manner. For example, interface device 404 may wirelessly connect to sound processor 104 via Bluetooth or any other suitable wireless communication protocol. Alternatively, interface device 404 may communicatively couple with sound processor 104 by way of any suitable wired connection.

Figure 5:
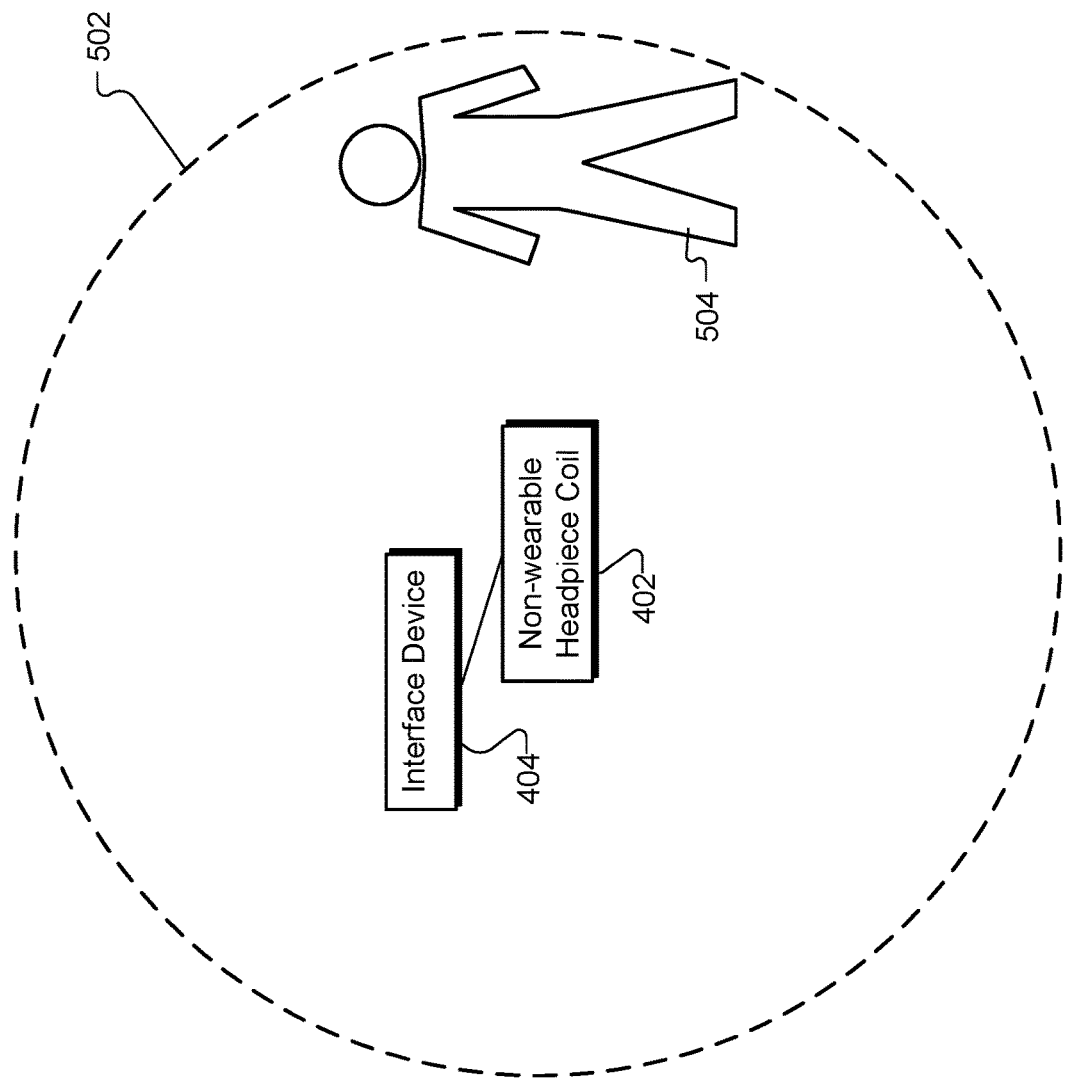
FIG. 5 illustrates an exemplary RF power transmission area in which an interface device is configured to provide RF power to a cochlear implant according to principles described herein.

Interface device 404 is configured to provide operating power to non-wearable coil 402 such that whenever the recipient is within a vicinity of interface device 404 and non-wearable coil 402, RF power and/or commands may be provided to cochlear implant 108 by way of wireless communication link 408. As such, unlike wearable headpiece coil 302, non-wearable coil 402 and cochlear implant coil 306 do not need to be provided at a predefined position with respect to each other to establish wireless communication link 408. Instead, the recipient may move to any arbitrary position within an RF power transmission area of non-wearable coil 402 and still receive RF power and/or commands by way of non-wearable coil 402. To illustrate, FIG. 5 shows an exemplary RF power transmission area 502 associated with non-wearable coil 402 and interface device 404. RF power transmission area 502 may have any suitable size as may serve a particular implementation. In the example shown in FIG. 5, a recipient 504 of cochlear implant 108 may move to any arbitrary position within RF power transmission area 502 and still have cochlear implant 108 receive RF power and/or commands by way of wireless communication link 408.

Figure 6:
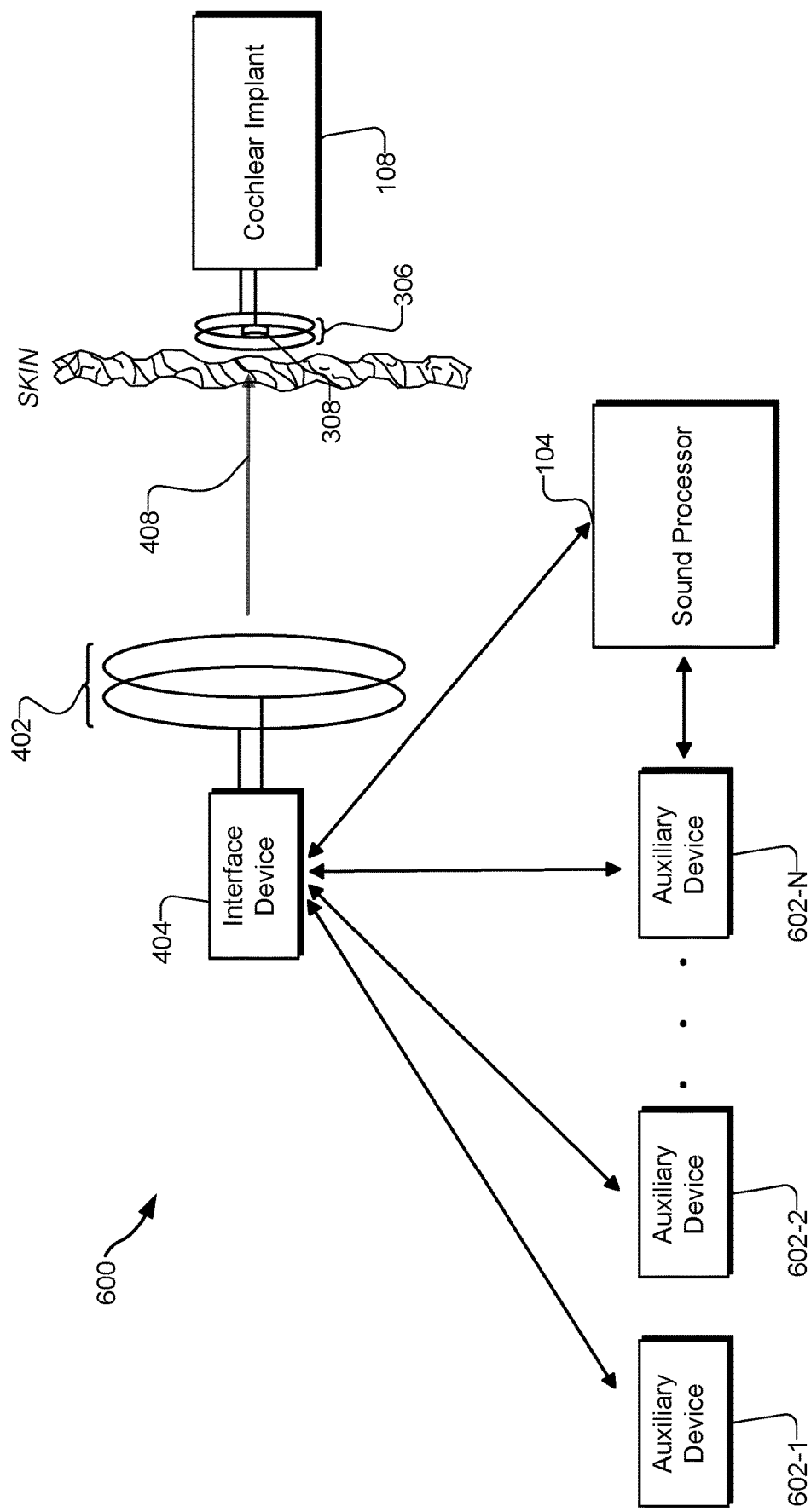
FIG. 6 illustrates another exemplary implementation in which a non-wearable coil is used to provide RF power to a cochlear implant according to principles described herein.

In certain examples, interface device 404 may be configured to communicatively couple to one or more auxiliary devices in addition to or alternatively to sound processor 104. To illustrate, FIG. 6 shows an exemplary implementation 600 in which interface device 404 is communicatively coupled to one or more auxiliary devices 602 (e.g., auxiliary devices 602-1 through 602-N) in addition to sound processor 104. Auxiliary devices 602 may be communicatively coupled directly to interface device 404 and/or may be indirectly communicatively coupled to interface device 404 by way of sound processor 104. Auxiliary devices 602 may include any suitable device that may provide an audio signal either directly or indirectly to interface device 404 to be passed along to cochlear implant 108. For example, auxiliary devices 602 may include one or more of a television, an alarm clock, a fire alarm system, a security alarm system, a media player, a computer, a mobile phone, an external microphone (e.g., a Roger Pen), etc.

To illustrate an example, auxiliary device 602-1 may be a television that sends (e.g., via Bluetooth) an audio signal (e.g., audio for a movie) to sound processor 104 to be delivered to cochlear implant 108 by way of non-wearable coil 402. Cochlear implant 108 may use the RF power received by way of non-wearable coil 402 to provide stimulation to the recipient such that the recipient perceives sounds associated with the audio signal. In certain alternative examples, one or more of auxiliary devices 602 may transmit an audio signal directly to interface device 404 without going through sound processor 104. In such examples, auxiliary device 602-1 may be configured to execute an application that facilitates auxiliary device 602-1 communicating directly with cochlear implant 108 via interface device 404 without going through sound processor 104.

In certain examples, interface device 404 may be implemented by a docking station for one or more of auxiliary devices 602 and/or sound processor 104. For example, interface device 404 may have dedicated portions (e.g., docking recesses) in which headpiece 106, sound processor 104, and/or any other suitable device is configured to dock. In certain examples, such a docking station may be configured to charge a battery of sound processor 104 while sound processor 104 is docked in the docking station.

In certain examples, interface device 404 may include a display device and/or a user input device that facilitate providing information to the recipient and receiving user input from the recipient. For example, interface device 404 may include a touch screen that provides information to the recipient and that is configured to receive touch inputs from the recipient. The information provided by way of the touch screen may include information regarding a charging status or battery level of sound processor 104, a connection status of sound processor 104 and/or one or more of auxiliary devices 602 to interface device 404, and/or any other suitable information associated with interface device 404. Through the touch screen, the recipient may provide touch inputs to configure interface device 404, to configure sound processor 104, and/or to manage the various devices communicatively coupled thereto.

Figure 7:
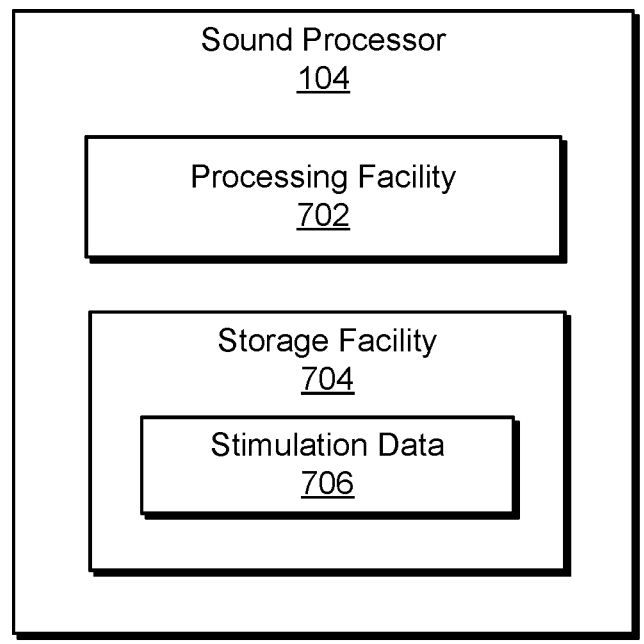
FIG. 7 illustrates exemplary components of a sound processor according to principles described herein.

While sound processor 104 is communicatively coupled to interface device 404, sound processor 104 may perform various operations to facilitate providing RF power and/or commands to cochlear implant 108 by way of non-wearable coil 402. FIG. 7 illustrates exemplary components of sound processor 104. It will be recognized that the components shown in FIG. 7 are merely representative of the many different components that may be included in sound processor 104 and that sound processor 104 may include additional or alternative components as may serve a particular implementation.

As shown in FIG. 7, sound processor 104 may include a processing facility 702 and a storage facility 704, which may be in communication with one another using any suitable communication technologies. Storage facility 704 may be configured to maintain stimulation data 706 generated and/or used by processing facility 702. Storage facility 704 may maintain additional or alternative data as may serve a particular implementation. One or more of facilities 702 and 704 may include a computing device or processor configured to perform one or more of the functions described herein. Processing facility 702 will now be described in more detail.

Processing facility 702 of sound processor 104 may be configured to operate in one or more modes depending on whether RF power is provided by way of wearable headpiece coil 302 or by way of non-wearable coil 402. For example, processing facility may operate in a first mode while wirelessly communicating with cochlear implant 108 by way of wearable headpiece coil 302 and processing facility 702 may operate in a second mode while wirelessly communicating with cochlear implant 108 by way of non-wearable coil 402. The first mode may be considered as a normal operation mode in which processing facility 702 receives and processes an audio signal presented to the recipient (e.g., an audio signal detected by microphone 102, an audio signal input by way of an auxiliary audio input port, etc.) while headpiece 106 is worn on the head of the recipient. The second mode, on the other hand, may correspond to a mode during which processing facility 702 is communicatively coupled to interface device 404 while interface device 404 provides RF power to cochlear implant 108 from a distance by way of non-wearable coil 402.

While processing facility 702 is coupled to interface device 404 and operating in the second mode, processing facility 702 may be configured to monitor ambient sound in an environment of the recipient. Processing facility 702 may monitor the ambient sound in any suitable manner. For example, processing facility 702 may use microphone 102 to detect the ambient sound in the environment surrounding the recipient.

Based on the monitored ambient sound, processing facility 702 may provide a command to cochlear implant 108 from a distance by way of non-wearable coil 402. The command may direct cochlear implant 108 to provide stimulation to the recipient to inform the recipient of the ambient sound. The RF power provided by way of non-wearable coil 402 powers cochlear implant 108 to apply the stimulation to the recipient. For example, the RF power may power cochlear implant 108 to at least apply a certain number of stimulation pulses (e.g., ten stimulation pulses) to one or more of electrodes 112. In certain examples, the stimulation provided to the recipient may cause the recipient to perceive the actual ambient sound. For example, if the ambient sound corresponds to a fire alarm, the stimulation provided to the recipient causes the recipient to perceive the sound of the fire alarm. Alternatively, the stimulation provided to the recipient may result in cochlear implant 108 providing a predefined alert informing the recipient of the detected ambient sound. For example, the stimulation provided to the recipient may cause the recipient to perceive a tone or a beep that informs the recipient of the fire alarm but that is audibly different than the fire alarm.

In certain examples, processing facility 702 may provide commands to cochlear implant 108 by way of non-wearable coil 402 based on an operating mode of cochlear implant 108. For example, while processing facility 702 is coupled to interface device 404 and operating in the second mode, cochlear implant 108 may operate in either a low-power non-stimulation mode or a stimulating mode. In the stimulating mode, processing facility 702 and cochlear implant 108 may operate according the same settings as during normal use except that RF power and/or commands are provided to cochlear implant 108 from a distance by way of non-wearable coil 402 as opposed to being provided by way of wearable headpiece coil 302. Additionally or alternatively, the stimulating mode may include processing facility 702 directing cochlear implant 108 to reduce a level of stimulation applied to the recipient such that the recipient can still monitor sound in an environment while headpiece 106 and wearable headpiece coil 302 are removed from the head of the recipient.

When cochlear implant 108 is in the low-power non-stimulation mode, cochlear implant 108 may not provide continual or consistent stimulation to the recipient. Instead, processing facility 702 may transmit a command to cochlear implant 108 by way of non-wearable coil 402 to apply stimulation only when the ambient sound has some predefined characteristic or combination of characteristics. For example, processing facility 702 may transmit a command to cochlear implant 108 by way of non-wearable coil 402 to apply stimulation only when the ambient sound has a predefined frequency, a predefined duration, and/or any other suitable characteristic. Additionally or alternatively, processing facility 702 may transmit a command to cochlear implant 108 by way of non-wearable coil 402 to apply stimulation only when the ambient sound is above a predefined threshold (e.g. a predefined volume threshold). To illustrate, processing facility 702 may monitor an environment surrounding the recipient while the recipient sleeps. If ambient sounds (e.g., traffic noises, air conditioning noises, etc.) occur that are below the predefined threshold, processing facility 702 may not transmit a command for cochlear implant 108 to stimulate the recipient. However, if an ambient sound (e.g., a fire alarm, an alarm clock ringing, a security alarm, a person yelling, etc.) occurs that is above the predefined threshold, processing facility 702 may be configured to transmit a command that directs cochlear implant 108 to stimulate the recipient so that the recipient perceives or is otherwise made aware of the ambient sound.

Additionally or alternatively, while cochlear implant 108 is in the low-power non-stimulation mode, no RF power may be provided to cochlear implant 108 by way of non-wearable coil 402 unless a predefined alert threshold is reached. For example, if the ambient sound in a vicinity of the recipient is below a predefined volume threshold, processing facility 702 may provide no RF power by way of non-wearable coil 402 to cochlear implant 108. However, when processing facility 702 determines that the ambient sound exceeds the predefined volume threshold, processing facility 702 may begin providing RF power to cochlear implant 108 by way of non-wearable coil 402 to power cochlear implant 108 to apply stimulation to the recipient thereby informing him/her of the ambient sound.

In certain examples, recipient 504 may experience tinnitus while wearable headpiece coil 302 is not attached to the head of recipient 504. In such examples, processing facility 702 may be further configured to provide a command to cochlear implant 108 by way of non-wearable coil 402 that facilitates reducing tinnitus experienced by the recipient and/or preventing the recipient from experiencing tinnitus. For example, while processing facility 702 is coupled to interface device 404 and operating in the second mode, processing facility 702 may be configured to transmit a command to cochlear implant 108 by way of non-wearable coil 402 to apply sub-threshold stimulation to one or more electrodes (e.g., electrodes 112) communicatively coupled to cochlear implant 108. As used herein, "sub-threshold stimulation" refers to stimulation that is below a threshold hearing level of recipient 504 (e.g., a level that does not result in providing a perception of sound to a recipient) and that reduces tinnitus experienced by recipient 504 and/or prevents recipient 504 from experiencing tinnitus (e.g., by preventing the continued and already occurring perception of noise ringing in the ears of a recipient).

Figure 8:
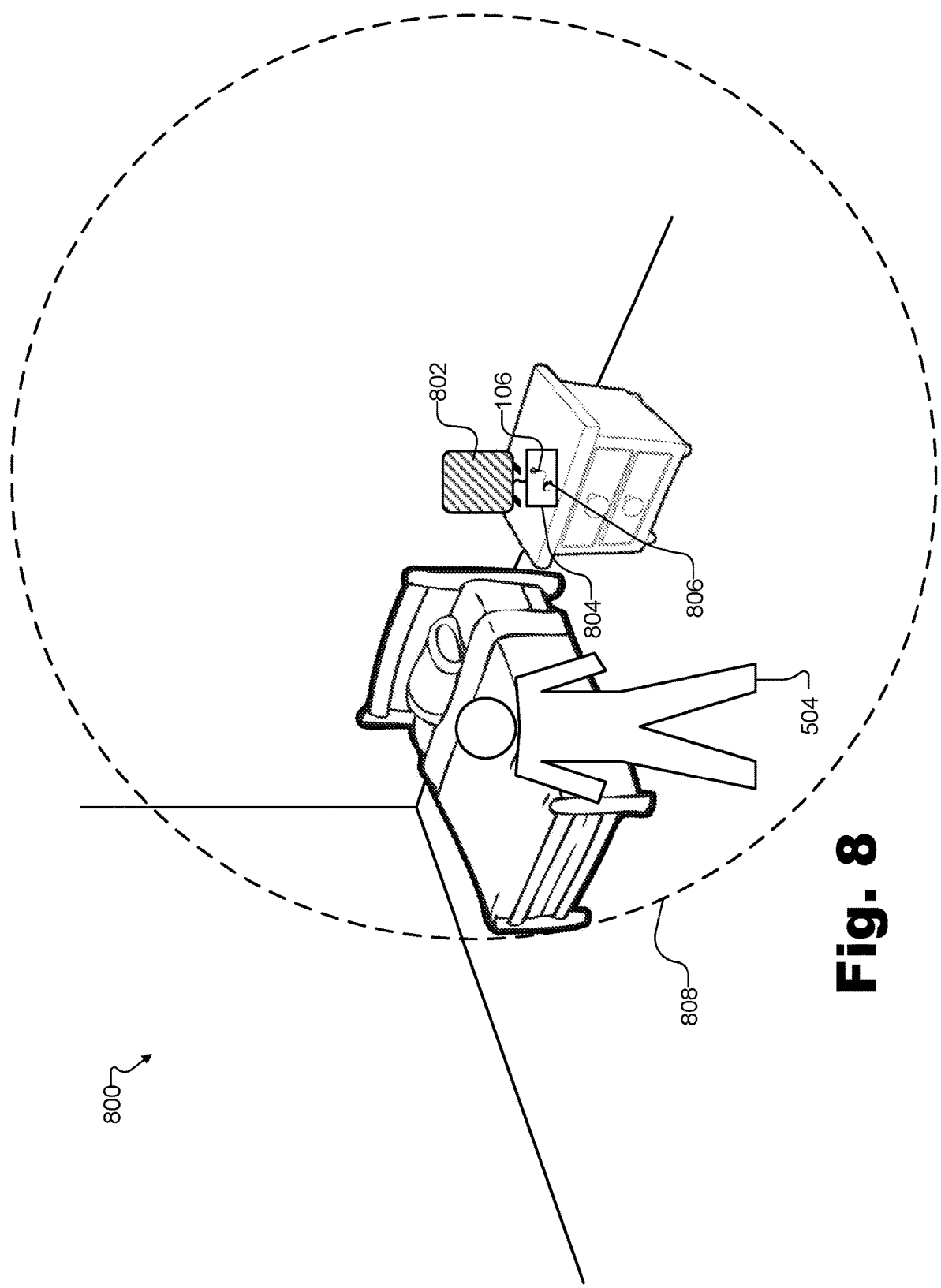
FIG. 8 illustrates an exemplary environment in which a non-wearable coil may be used to provide RF power to a cochlear implant according to principles described herein.

FIG. 8 shows an exemplary environment 800 in which a non-wearable coil may be provided. As shown in FIG. 8, a non-wearable coil 802 is communicatively coupled to an interface device 804 in a bedroom associated with recipient 504. In the example shown in FIG. 8, headpiece 106 is removed from the head of recipient 504 and is docked with interface device 804. As shown in FIG. 8, headpiece 106 is communicatively coupled to a BTE unit 806, which may house sound processor 104 and/or a battery. While headpiece 106 and BTE unit 806 are docked with interface device 804, interface device 804 may be configured to charge the battery provided within BTE unit 806 in any suitable manner. In addition, interface device 804 is configured to transmit commands from sound processor 104 and/or RF power to a cochlear implant of recipient 504. In the example shown in FIG. 8, non-wearable coil 802 is provided with operating power and has a size such that the RF power and commands may be provided anywhere within an RF power transmission area 808. As such, as long as recipient 504 is within RF power transmission area 808, RF power and/or commands may be provided to cochlear implant 108 from a distance by way of non-wearable coil 802.

In certain examples, a charging pad may be configured to inductively recharge a battery associated with sound processor 104. Such a charging pad may include a coil that may be used as a non-wearable coil to transmit RF power and/or commands from a distance to cochlear implant 108. In such examples, the charging pad may be configured switch between a charging mode and an RF power transmitting mode. In the charging mode, the coil in the charging pad may be configured to operate at a first frequency to inductively charge the battery associated with sound processor 104 when, for example, a BTE unit that houses the battery and sound processor 104 is placed on the charging pad. In the RF power transmitting mode, the coil provided in the charging pad may be reconfigured, in any suitable manner, to operate at a second frequency that facilitates transmission of the RF power and/or commands by way of the coil in the charging pad to cochlear implant 108 from a distance.

In certain alternative examples, the systems and methods described herein may be used in conjunction with a fully implanted cochlear implant system in which a sound processor and a battery are fully implanted within the recipient. In such examples, a non-wearable coil (e.g., non-wearable coil 802) may be used to provide RF power and/or commands to the implanted components. To illustrate, in certain examples, the implanted sound processor may enter a hibernation mode when the recipient is sleeping. During such a hibernation mode, the implanted battery may not be used to power the fully implanted cochlear implant system. Instead, RF power may be provided by way of a non-wearable coil in any suitable manner such as described herein to power the cochlear implant and facilitate notifying the recipient of an ambient sound or any other alert or notification. In so doing, it may be possible to reduce the number of times that the implanted battery needs to be recharged, thereby extending the operational life of the implanted battery.

Figure 9:
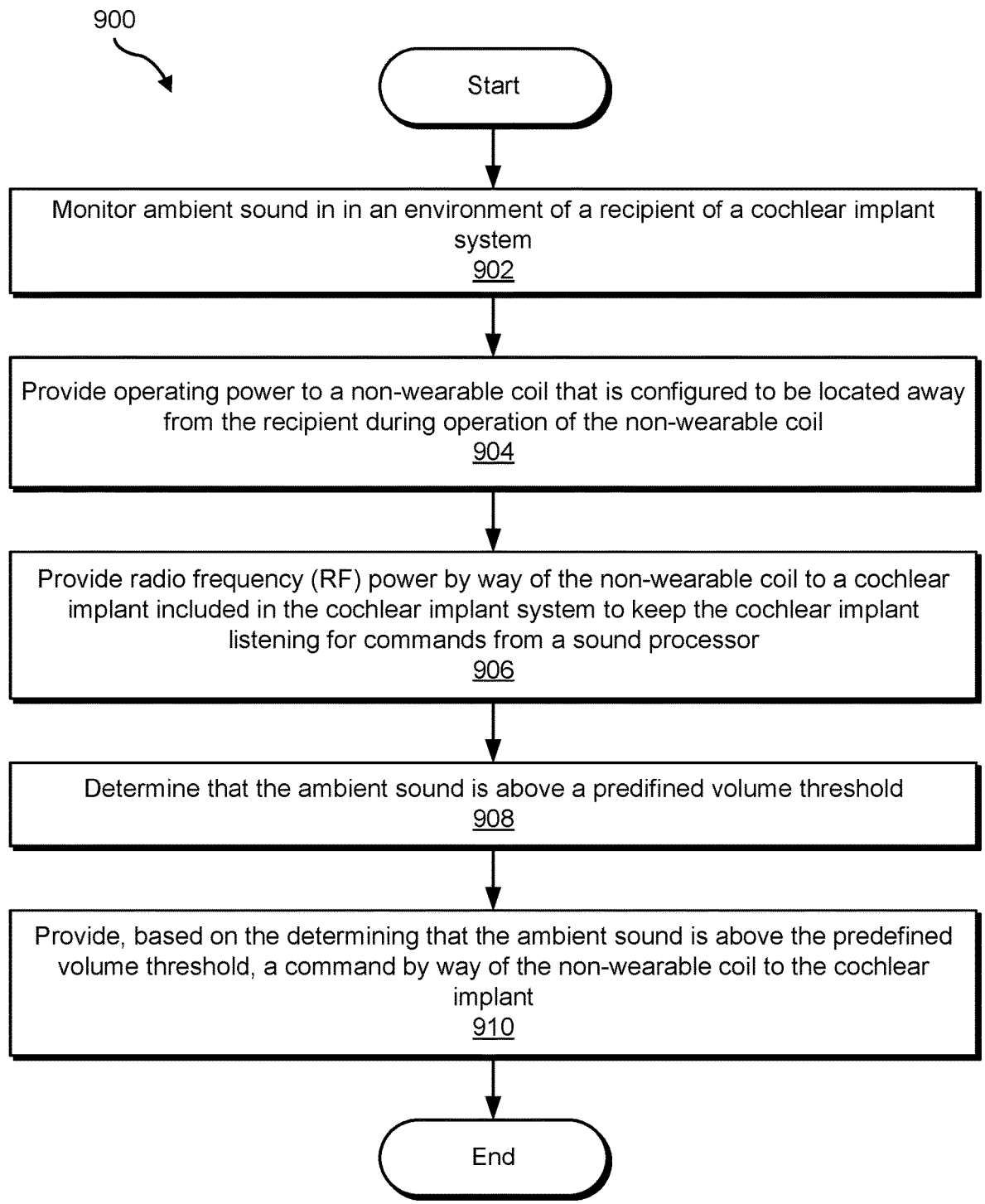
FIG. 9 illustrates an exemplary method for utilizing a non-wearable coil to remotely power a cochlear implant from a distance according to principles described herein.

FIG. 9 illustrates an exemplary method 900. While FIG. 9 illustrates exemplary steps according to one embodiment, other embodiments may omit, add to, reorder, and/or modify any of the steps shown in FIG. 9. One or more of the steps shown in FIG. 9 may be performed by sound processor 104, interface device 404, and/or any implementation thereof.

In step 902, a sound processor (e.g., sound processor 104), which is included in a cochlear implant system (e.g., system 100) and is communicatively coupled to an interface device (e.g., interface device 404), monitors ambient sound in an environment of a recipient of the cochlear implant system. The sound processor monitors the ambient sound during a time period in which a wearable headpiece coil configured to be worn on a head of the recipient of the cochlear implant system is detached from the head of the recipient. Step 902 may be performed in any of the ways described herein.

In step 904, the interface device provides operating power to a non-wearable coil that is configured to be located away from the recipient during operation of the non-wearable coil. In certain examples, the interface device may be configured to generate and provide the operating power to the non-wearable coil. Additionally or alternatively, the sound processor may provide the operating power to the interface device, which then passes the operating power to the non-wearable coil. Step 904 may be performed in any of the ways described herein.

In step 906, the interface device provides RF power by way of the non-wearable coil to a cochlear implant included in the cochlear implant system to keep the cochlear implant listening for commands from the sound processor. For example, the RF power may be provided from the non-wearable coil to the cochlear implant over a uni-directional communication link. Step 906 may be performed in any of the ways described herein.

In step 908, the sound processor determines that the ambient sound is above a predefined volume threshold. Step 908 may be performed in any of the ways described herein.

In step 910, the sound processor provides, based on the determining that the ambient sound is above the predefined volume threshold, a command by way of the non-wearable coil to the cochlear implant. The command may instruct the cochlear implant to provide stimulation to the recipient. Step 910 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
  a sound processor configured to wirelessly communicate, while operating in a first mode, with a cochlear implant by way of a wearable headpiece coil configured to be worn on a head of a recipient of the cochlear implant;
  a non-wearable coil; and
  an interface device configured to provide operating power to the non-wearable coil and communicatively couple to the sound processor while the sound processor is operating in a second mode,
  wherein:
    while the sound processor is coupled to the interface device and operating in the second mode, the non-wearable coil is configured to provide radio frequency (RF) power to the cochlear implant to keep the cochlear implant listening for commands from the sound processor;
    the sound processor is further configured to:
      detect, while coupled to the interface device and operating in the second mode, an ambient sound in an environment of the recipient; and
      transmit a command to the cochlear implant by way of the non-wearable coil, the command instructing the cochlear implant to provide stimulation to the recipient based on the ambient sound detected in the environment of the recipient; and
    the stimulation applied to the recipient is configured to cause the recipient to perceive a predefined notification that is audibly different than the ambient sound and that informs the recipient of the ambient sound.

2. The system of claim 1, wherein the sound processor is configured to transmit the command to the cochlear implant by way of the non-wearable coil when the ambient sound in the environment is above a predefined threshold.

3. The system of claim 2, wherein the RF power provided by way of the non-wearable coil powers the cochlear implant to apply the stimulation to the recipient.

4. The system of claim 1, wherein, while the sound processor is coupled to the interface device and operating in the second mode, the sound processor is configured to receive an audio signal from an auxiliary device communicatively coupled to the sound processor.

5. The system of claim 4, wherein the RF power provided by way of the non-wearable coil powers the cochlear implant to apply stimulation representative of the audio signal to the recipient.

6. The system of claim 1, wherein, while the sound processor is coupled to the interface device and operating in the second mode:
  the sound processor is configured to transmit an additional command to the cochlear implant by way of the non-wearable coil to apply sub-threshold stimulation to one or more electrodes communicatively coupled to the cochlear implant;
  the sub-threshold stimulation is provided at a level that is below a threshold hearing level of the recipient such that the sub-threshold stimulation does not provide the recipient with a perception of sound; and
  the sub-threshold stimulation at least one of reduces tinnitus experienced by the recipient and prevents the recipient from experiencing tinnitus.

7. The system of claim 1, wherein:
  the wearable headpiece coil is provided as part of a wearable headpiece that includes a headpiece magnet;
  the headpiece magnet is configured to interact with a cochlear implant magnet provided within the cochlear implant so as to maintain the wearable headpiece at a predefined position with respect to the cochlear implant while the headpiece is worn on the head of the recipient, and
  the wearable headpiece is configured to provide additional RF power to the cochlear implant by way of the wearable headpiece coil while the sound processor operates in the first mode.

8. The system of claim 7, wherein the interface device is a docking station configured to charge a battery associated with the wearable headpiece while the wearable headpiece is removed from the head of the recipient and is docked in the docking station.

9. The system of claim 1, wherein the interface device is configured to perform uni-directional communication with the cochlear implant by way of the non-wearable coil.

10. The system of claim 1, wherein:
  the non-wearable coil has a first size and the cochlear implant coil has a second size; and
  the first size is larger than the second size.

11. A system comprising:
  a cochlear implant that is implanted within a recipient and includes a cochlear implant coil and a cochlear implant magnet, the cochlear implant operating in accordance with radio frequency (RF) power received by way of the cochlear implant coil;
  a wearable headpiece that includes a headpiece magnet and a wearable headpiece coil, the headpiece magnet configured to interact with the cochlear implant magnet so as to maintain the wearable headpiece at a predefined position with respect to the cochlear implant while the wearable headpiece is worn on a head of the recipient, the wearable headpiece configured to provide the RF power to the cochlear implant by way of the headpiece coil while the wearable headpiece is worn on the head of the recipient at the predefined position and while the wearable headpiece coil is communicatively coupled to the cochlear implant coil;
  a non-wearable coil configured to communicatively couple with the cochlear implant coil;

an interface device configured to provide operating power to the non-wearable coil such that the non-wearable coil provides additional RF power to the cochlear implant while the non-wearable coil is communicatively coupled to the cochlear implant coil; and a sound processor configured to:
  operate in a first mode while the headpiece coil is communicatively coupled to the cochlear implant coil;
  detect, while coupled to the interface device and operating in a second mode, an ambient sound in an environment of the recipient; and
  transmit a command to the cochlear implant by way of the non-wearable coil, the command instructing the cochlear implant to provide stimulation to the recipient based on the ambient sound detected in the environment of the recipient,
wherein the stimulation applied to the recipient is configured to cause the recipient to perceive a predefined notification that is audibly different than the ambient sound and that informs the recipient of the ambient sound.

12. The system of claim 11,
wherein the interface device is further configured to:
  communicatively couple to the sound processor while the sound processor is operating in the second mode;
  receive, from the sound processor while the sound processor is operating in the second mode, the command from the sound processor; and
  provide the additional RF power and the command to the cochlear implant by way of the non-wearable coil.

13. The system of claim 11, wherein the interface device is further configured to:
  communicatively couple to one or more auxiliary devices;
  receive, from the one or more auxiliary devices, an audio signal to be represented to the recipient by way of the cochlear implant; and
  provide the additional RF power and an additional command to the cochlear implant by way of the non-wearable coil, the additional command directing the cochlear implant to apply stimulation representative of the audio signal to the recipient.

14. The system of claim 13, wherein:
  the interface device is configured to communicatively couple to the wearable headpiece while the wearable headpiece is removed from the recipient;
  the wearable headpiece is communicatively coupled to a sound processor; and
  the one or more auxiliary devices communicatively couple to the interface device by way of the sound processor.

15. A method comprising:
monitoring, by a sound processor included in a cochlear implant system while the sound processor is communicatively coupled to an interface device during a time period in which a wearable headpiece coil configured to be worn on a head of a recipient of the cochlear implant system is detached from the head of the recipient, ambient sound in in an environment of the recipient, the interface device configured to
  provide operating power to a non-wearable coil, and
  provide radio frequency (RF) power by way of the non-wearable coil to a cochlear implant included in the cochlear implant system to keep the cochlear implant listening for commands from the sound processor;
determining, by the sound processor, that the ambient sound is above a predefined volume threshold; and
providing, by the sound processor based on the determining that the ambient sound is above the predefined volume threshold, a command by way of the non-wearable coil to the cochlear implant, the command instructing the cochlear implant to provide stimulation to the recipient,
wherein the stimulation applied to the recipient is configured to cause the recipient to perceive a predefined notification that is audibly different than the ambient sound and that informs the recipient of the ambient sound.

16. The method of claim 15, further comprising directing, by the sound processor, a battery of the cochlear implant system to provide the operating power to the interface device to be passed by the interface device to the non-wearable coil.

17. The method of claim 15, wherein the stimulation applied to the recipient based on the command further causes the recipient to perceive the ambient sound.

* * * * *